(12) United States Patent
Finlay et al.

(10) Patent No.: US 9,670,443 B2
(45) Date of Patent: Jun. 6, 2017

(54) TISSUE ENGINEERED CONSTRUCTS

(71) Applicants: University of Leeds, Leeds, Yorkshire (GB); Xiros Limited, Leeds, Yorkshire (GB)

(72) Inventors: Scott Finlay, Cardiff (GB); Bahaa Botros Seedhom, Leeds (GB)

(73) Assignees: UNIVERSITY OF LEEDS, Leeds, Yorkshire (GB); XIROS LIMITED, Leeds, Yorkshire (GB)

(*) Notice: Subject to any disclaimer, the term of this patent is extended or adjusted under 35 U.S.C. 154(b) by 0 days.

(21) Appl. No.: 14/315,108

(22) Filed: Jun. 25, 2014

(65) Prior Publication Data
US 2015/0376560 A1  Dec. 31, 2015

(51) Int. Cl.
| | | |
|---|---|---|
| A61L 27/38 | (2006.01) |
| C12M 3/00 | (2006.01) |
| A61K 35/12 | (2015.01) |
| C12M 1/12 | (2006.01) |
| C12N 5/071 | (2010.01) |
| C12N 5/077 | (2010.01) |
| A61L 27/18 | (2006.01) |
| A61L 27/56 | (2006.01) |

(52) U.S. Cl.
CPC ............ *C12M 21/08* (2013.01); *A61K 35/12* (2013.01); *A61L 27/18* (2013.01); *A61L 27/3817* (2013.01); *A61L 27/3852* (2013.01); *A61L 27/56* (2013.01); *C12M 25/14* (2013.01); *C12N 5/0655* (2013.01); *C12N 5/0697* (2013.01); *A61L 2430/24* (2013.01)

(58) Field of Classification Search
None
See application file for complete search history.

(56) References Cited

U.S. PATENT DOCUMENTS

| | | | |
|---|---|---|---|
| 6,454,811 B1 * | 9/2002 | Sherwood et al. | 623/23.76 |
| 7,772,000 B2 | 8/2010 | Hauselmann | |
| 8,600,801 B2 * | 12/2013 | Brandt | G06Q 30/02 379/266.01 |
| 2002/0106625 A1 * | 8/2002 | Hung | C12M 21/08 435/1.1 |
| 2012/0313284 A1 * | 12/2012 | Detamore et al. | 264/122 |
| 2013/0030528 A1 | 1/2013 | Chen et al. | |

FOREIGN PATENT DOCUMENTS

| | | |
|---|---|---|
| CN | 201284346 | 8/2009 |
| WO | 01/68800 | 9/2001 |
| WO | WO 2007/007106 * | 1/2007 |
| WO | WO 2007/115336 * | 10/2007 |
| WO | 2009/047045 | 4/2009 |
| WO | 2011/121377 | 10/2011 |
| WO | 2013/152036 | 10/2013 |

OTHER PUBLICATIONS

VWR, Polystyrene, Disposable, Sterile Petri Dishes, retrieved from the internet Jan. 7, 2015:us.vwr.com/store/catalog/product.jsp-?product_id=8872140.*
The Engineering ToolBox, Modulus of Elasticity, retrieved from the internet, Jan. 7, 2016: www.engineeringtoolbox.com/young-modulus-d_417.html.*
Kisiday, John D. et al., "Effects of dynamic compressive loading on chondrocyte biosynthesis in self-assembling peptide scaffolds," Journal of Biomechanics, vol. 37, 2004, p. 595-604.
Waldman, Stephen D. et al., "Long-Term Intermittent Compressive Stimulation Improves the Composition and Mechanical Properties of Tissue-Engineered Cartilage," Tissue Engineering, vol. 10, No. 9/10, 2004, p. 1323-1331.
Lima, E. G. et al., "The beneficial effect of delayed compressive loading on tissue-engineered cartilage constructs cultured with TGF-Beta3," Osteoarthritis and Cartilage, vol. 15, No. 9, 2007, p. 1025-1033.
Butler, David L. et al., "The Impact of Biomechanics in Tissue Engineering and Regenerative Medicine," Tissue Engineering, Part B, vol. 15, No. 4, 2009, p. 477-484.
Mauck, R. L. et al., "The role of cell seeding density and nutrient supply for articular cartilage tissue engineering with deformational loading," Osteoarthritis and Cartilage, vol. 11, 2003, p. 879-890.
Tran, Scott C. et al., "Effect of a Mechanical Stimulation Bioreactor on Tissue Engineered, Scaffold-Free Cartilage," Biotechnology and Bioengineering, vol. 108, No. 6, 2011, p. 1421-1429.
MacKay, Alastair M. et al., "Chondrogenic Differentiation of Cultured Human Mesenchymal Stem Cells from Marrow," Tissue Engineering, vol. 4, No. 4, 1998, Mary Ann Liebert, Inc.
Mauck, Robert L. et al., "Functional Tissue Engineering of Articular Cartilage Through Dynamic Loading of Chondrocyte-Seeded Agarose Gels," Journal of Biomechanical Engineering, Jun. 2000, vol. 122, p. 252-260.
Kim, Hubert T. et al., "A Peek Into the Possible Future of Management of Articular Cartilage Injuries: Gene Therapy and Scaffolds for Cartilage Repair," Journal of Orthopaedic & Sports Physical Therapy, vol. 36, No. 10, Oct. 2006, p. 765-773.

(Continued)

*Primary Examiner* — Thane Underdahl
*Assistant Examiner* — Yvonne Pyla
(74) *Attorney, Agent, or Firm* — Kirkton McConkie; Evan R. Witt

(57) ABSTRACT

A method of forming an implantable tissue engineered construct, a bioreactor for forming a tissue engineered construct, and a tissue engineered construct itself are disclosed The method includes seeding a scaffold with cells to form a tissue construct; locating the tissue construct in a space defined by a tissue construct support element; locating the tissue construct support element within a bioreactor; and operating a load applicator of the bioreactor to apply a cyclical compressive mechanical load to the tissue construct, to stimulate the deposition of tissue matrix in the tissue construct, in which the tissue construct, the tissue construct support element and the load applicator are arranged so that the load applicator can at least initially contact both the tissue construct and the tissue construct support element, so that at least part of a total load generated by the load applicator is borne by the tissue construct support element.

19 Claims, 10 Drawing Sheets

(56) References Cited

OTHER PUBLICATIONS

Luo, Z-J et al., "Light and low-frequency pulsatile hydrostatic pressure enhances extracellular matrix formation by bone marrow mesenchymal cells: an in-vitro study with special reference to cartilage repair," Proceedings of the Institution of Mechanical Engineers, Part H: Journal of Engineering in Medicine 2007, vol. 221, p. 499-507.

Schulz, Ronny M. et al. "Development and Validation of a Novel Bioreactor System for Load-and Perfusion-Controlled Tissue Engineering of Chondrocyte-Constructs," Biotechnology and Bioengineering, vol. 101, No. 4, Nov. 1, 2008, pp. 714-728.

Stoffel, Marcus et al. "Bioreactor cultivation and remodelling simulation for cartilage replacement material," Medical Engineering & Physics, vol. 34, 2012, pp. 56-63.

Mauck, Robert L. et al. "Functional Tissue Engineering of Articular Cartilage Through Dynamic Loading of Chondrocyte-Seeded Agarose Gels," Transactions of the ASME, vol. 122, Jun. 2000, pp. 252-260.

Bian, Liming et al., "Dynamic Compressive Loading Enhances Cartilage Matrix Synthesis and Distribution and Suppresses Hypertrophy in hMSC-Laden Hyaluronic Acid Hydrogels," Tissue Engineering: Part A, vol. 18, No. 7 and 8, 2012, pp. 715-724.

Kock, Linda et al., "Tissue engineering of functional articular cartilage: the current status," Cell and Tissue Research, Springer, Berlin, DE, vol. 347, No. 3, Oct. 27, 2011, pp. 613-627.

Verteramo, A. et al., "Effect of a single impact loading on the structure and mechanical properties of articular cartilage," Journal of Biomechanics, Pergamon Press, New York, NY, vol. 40, No. 16, Jan. 1, 2007, pp. 3580-3589.

\* cited by examiner

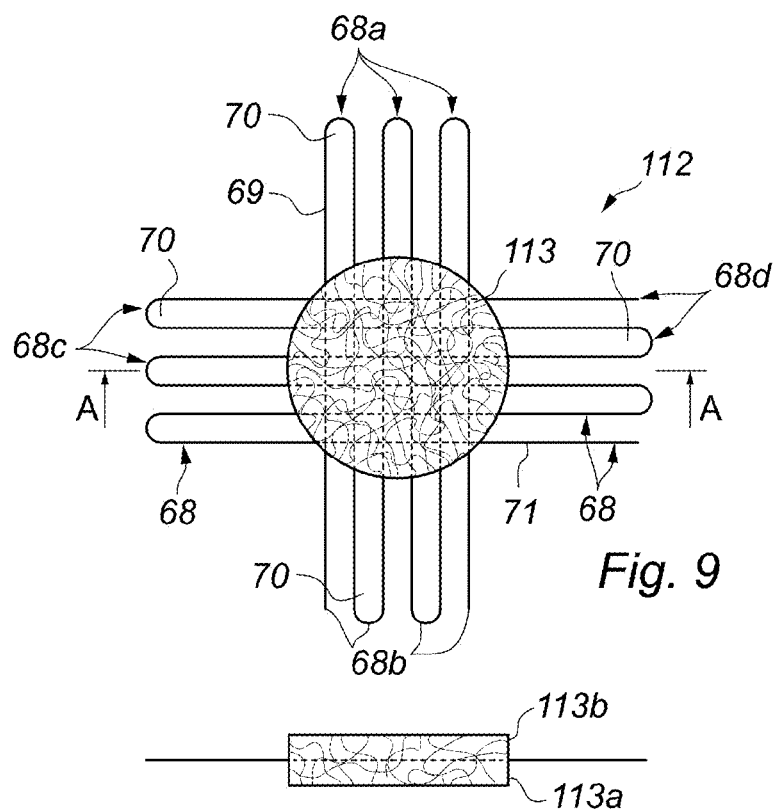
Fig. 9
Fig. 9a
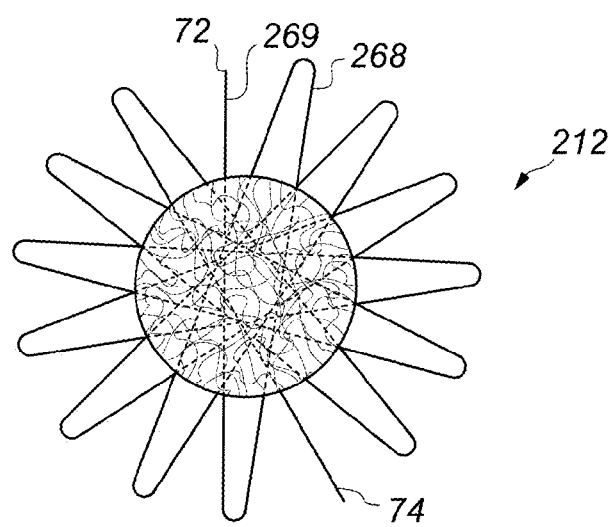
Fig. 10

TISSUE ENGINEERED CONSTRUCTS

FIELD OF THE INVENTION

The present invention relates to a method of forming a tissue engineered construct, a bioreactor for forming a tissue engineered construct, and to a tissue engineered construct itself. In particular, but not exclusively, the present invention relates to a method of forming a tissue engineered construct involving the application of a cyclical mechanical load to a tissue construct comprising a scaffold which has been seeded with cells.

BACKGROUND OF THE INVENTION

In the field of tissue engineering, it is well known that tissue constructs can be produced which are implantable in the human (or animal) body, to aid in the repair of damaged tissue. The tissue in question may, for example, have experienced trauma or be the subject of a degenerative condition. The tissue constructs comprise scaffolds which have typically been seeded with cells taken from a patient (autogenous cells), or from a suitable donor (allogenic cells), and are implanted in the body in the region of the damaged tissue. The construct may replicate at least part of the function of the damaged tissue, and/or may promote the growth of natural tissue in the damaged region.

A particular focus of recent research has concerned attempts to form tissue engineered constructs for cartilage repair, which can be implanted in the body of a patient who has experienced damage to, or degeneration of, natural cartilage tissue. Examples of the former would be patients who have experienced cartilage injury associated with common joint injuries such as to the anterior cruciate ligament (ACL).

Cartilage damage can eventually lead to osteoarthritis, causing pain and reduced joint mobility, seriously compromising the affected individual's quality of life. It is well recognised that cartilage has a poor capacity for spontaneous self-repair, in part because of its low cellularity and the lack of vascular and lymphatic systems necessary for efficient healing. In addition, any neo-tissue that is deposited is likely to be destroyed by the stresses acting within joints during daily activities, because it is mechanically weak. Intervention is required to maintain quality of life. However, so far, surgical treatments for articular cartilage defects have not been consistently effective in preventing the recurrence of damage.

One potential strategy for repairing cartilage is the implantation of in-vitro produced cartilage constructs that have similar matrix composition, and mechanical properties, to those of the surrounding native cartilage. The principles of tissue engineering would be followed in creating such cartilage constructs, where appropriate mechanical stimulation would be applied onto cells seeded onto a suitable 3D scaffold to promote a chondrocyte-like phenotype and matrix. It is well documented that biochemical stimulation is a pre-requisite for successful differentiation/re-differentiation of cells and desired tissue deposition. Mechanical stimulation is also a highly influential factor in the formation of tissue, especially musculoskeletal tissue.

In order for mechanical loading to elicit a desired mechanotransductive effect on a construct, it is considered that the following criteria should be met: 1) the scaffold should be sufficiently compliant and populated by viable cells with a chondrocyte-like phenotype and initially surrounded by sufficient extracellular matrix (ECM) so that, when loaded, the scaffold will deform and the applied force will be transmitted through the matrix to the cells via appropriate integrins, leading to further deposition and remodelling of the ECM resulting in a cartilage-like construct; and 2) to achieve the above, the values of compressive strain applied on to the constructs should be within the physiological range, which maintain the native tissue's functional properties and therefore likely to induce the desired anabolic effects.

However, to date, the application of compressive loading has had limited success in creating mechanically functional constructs that are suitable to be implanted. It has been suggested that, because these constructs had moduli that were significantly lower than those of the surrounding native cartilage, they would deform under joint loading by a greater amount post-implantation, generating excessive shear at the construct-tissue interface, impeding integration. In addition, such constructs have been considered unable to withstand the combination of high compressive and shear stresses arising in the joint in question.

One prior technique involving the application of pulsatile hydrostatic pressure (PHP) is discussed in the paper by Luo and Seedhom entitled "Light and low-frequency pulsative hydrostatic pressure enhances extracellular matrix formation by bone marrow mesenchymal cells: An in-vitro study with special reference to cartilage repair", published in the Proceedings of the Institution of Mechanical Engineers, Vol. 221, Part H: Journal of Engineering in Medicine, May 2007. The technique involves forming circular pads of non-woven filamentous material, subjecting the pads to plasma treatment to confer hydrophilicity, and sterilising the pads with gamma irradiation, to form scaffolds. Ovine bone marrow cells are then seeded on to the scaffolds, and the resulting cell-scaffold constructs are cultured in a chondrogenic medium. The cell-scaffold constructs are then subjected to (PHP) of a fixed, low magnitude of 0.1 MPa, and with a sinusoidal wave pattern of a fixed, low frequency of 0.25 Hz, for 30 minutes every day for 10 days. This stimulates tissue matrix deposition in the cell-scaffold construct. Biochemical assays demonstrated that DNA content in the group of PHP constructs subjected to this technique was 1.5 times greater than in a control group at day 10. However, it has been found that the tissue matrix formed does not provide the construct with sufficient modulus, compared to that of natural cartilage tissue, so that the scaffold will not have sufficient stiffness to form an effective implant.

Another prior technique involving the application of compressive loading is disclosed in the paper by Mauck et al entitled "Functional tissue engineering of articular cartilage through dynamic loading of chondrocyte-seeded agarose gels", published in the Journal of Biomechanical Engineering, 252/Vol. 122, June 2000. The technique involves forming constructs by seeding hydrogel discs with cells derived from harvested bovine articular chondrocytes, and loading the cell-seeded construct discs using a bioreactor driven by a motor via a cam arrangement and monitoring the load applied with a load cell. The discs are loaded dynamically in unconfined compression with a peak-to-peak compressive strain of 10%, for an hour at a frequency of 1 Hz three times per day, five days per week, over a four week period. This stimulates tissue matrix deposition in the constructs. Whilst results demonstrated that such dynamically loaded constructs yielded an increase in equilibrium aggregate modulus over free swelling controls after 28 days of loading, it has again been found that the tissue matrix formed does not provide the constructs with sufficient modulus to form an effective implant.

If constructs with mechanical properties comparable to those of the native cartilage could be implanted, they would be more likely to survive the rigors of the mechanical environment within the joint in question, to integrate with the surrounding native cartilage, and to produce long term repair. However, to date, none of the techniques employed have produced cartilage constructs having an acceptable elastic modulus (stiffness) and/or yield strength to adequately replicate native cartilage tissue.

The problems discussed above are not restricted to cartilage tissue, and so apply equally to other body tissues.

It is an object of the present invention to obviate or mitigate at least one of the foregoing disadvantages.

SUMMARY OF THE INVENTION

According to a first aspect of the present invention, there is provided a method of forming an implantable tissue engineered construct, the method comprising the steps of:
  seeding a scaffold with cells to form a tissue construct;
  locating the tissue construct in a space defined by a tissue construct support element;
  locating the tissue construct support element within a bioreactor; and
  operating a load applicator of the bioreactor to apply a cyclical compressive mechanical load to the tissue construct, to stimulate the deposition of tissue matrix in the tissue construct;
  in which the tissue construct, the tissue construct support element and the load applicator are arranged so that the load applicator can at least initially contact both the tissue construct and the tissue construct support element, so that at least part of a total load generated by the load applicator is borne by the tissue construct support element.

According to a second aspect of the present invention, there is provided a bioreactor for use in forming an implantable tissue engineered construct, the bioreactor comprising:
  a tissue construct support element defining a space which can receive a tissue construct comprising a scaffold which has been seeded with cells; and
  a load applicator which is operable to apply a cyclical compressive mechanical load to the tissue construct to stimulate the deposition of tissue matrix in the tissue construct;
  in which the load applicator can at least initially contact both the tissue construct and the tissue construct support element, so that at least part of a total load generated by the load applicator is borne by the tissue construct support element.

Arranging the load applicator so that it can at least initially contact both the tissue construct and the tissue construct support element provides the advantage that at least part of a total load generated by the load applicator is (at least initially) borne by the tissue construct support element. In this way, the present invention ensures that the tissue construct is not initially subjected to high strains (and so stresses), which could damage cells and deposited tissue in the construct scaffold, and impair the deposition of further tissue matrix. However, sufficient strain is applied to stimulate anabolic effects, and the deposition of additional tissue matrix. In addition, the present invention provides the ability to operate the load applicator under a consistent loading regime, and in particular does not require that the maximum total load imparted by the load applicator be varied during the tissue engineering procedure within the bioreactor.

The present invention may facilitate the creation of tissue engineered constructs in-vitro (in the bioreactor), by the use of cyclic compressive loading that effectively adapts based on the physical properties of the construct itself. Specifically, as a tissue construct increases its thickness and stiffness (by the deposition of matrix by residing cells), the strain and stress applied to the construct increases accordingly. This is believed to provide continued suitable cellular stimulation throughout culture, to cause the constructs to reach desirable stiffness, and therefore be functional as a tissue replacement/implant.

The method may be a method of forming an implantable tissue engineered construct in-vitro.

The tissue construct support element may have an elastic modulus (stiffness) which is greater than an elastic modulus of the tissue construct prior to commencement of the application of the mechanical load, and which may be considerably greater. The support element may be resiliently deformable, and may be capable of resiliently supporting compressive mechanical loading resulting in strains of at least around 1%, and optionally up to around 5%. The support element may be capable of resiliently supporting compressive mechanical loading resulting in strains in the range of around 1% to around 5%, optionally in the range of around 3% to around 4%. It will be understood that a strain of 3% (in compression) is a strain which results in a reduction in dimension of the support element (in the direction of application of load) of 3%, relative to its starting, unloaded dimension. The support element may have a compressive elastic modulus of at least around 2 MPa, may have a modulus of at least around 2.5 MPa, and may have a modulus of around 2.64 MPa. The support element may have a compressive elastic modulus in the range of around 1 MPa to around 5 MPa. Materials having such a modulus of elasticity are relatively compressible, and may be particularly suited for forming the support element. However, other materials having higher moduli of elasticity may be employed. The tissue construct support element may have an elastic modulus which is at least around 10 times greater than an elastic modulus of the tissue construct prior to commencement of the application of the mechanical load, and may have an elastic modulus which is up to around 25 times greater.

The support element may be of a polymeric material. The support element may be of an elastomeric material. The support element may be a silicone material, i.e. a polymeric material comprising silicon. The support element is preferably of a material which is biocompatible.

The tissue construct may initially experience compressive mechanical loading resulting in strains of at least around 10%, optionally at least 20%, optionally at least around 30%.

The tissue construct may be located in the space defined by said support element so that it protrudes beyond an upper surface, or an upper extent, of the support element. The tissue construct may comprise an upper surface, and the upper surface of the tissue construct may be located above the upper surface/extent of the support element.

The tissue construct support element may have a maximum thickness, and the tissue construct may have a maximum thickness which is greater than that of the support element. The tissue construct support element may have a mean thickness of its cross-section, and the tissue construct may have a mean thickness of its cross-section which is greater than that of the support element.

The tissue construct support element may comprise an aperture extending through the support element, and the aperture may define the space. The aperture may extend through the support element in a direction from a top to a bottom of the element. The support element may comprise an upper surface and a lower surface, and the aperture may comprise: an upper opening provided in the upper surface of the support element; a lower opening provided in the lower surface of the support element; and a passage extending between the upper and lower openings.

The tissue construct support element may comprise a recess which may extend part-way through the support element, the recess defining the space. The recess may extend from the top of the support element part way through the element towards a bottom of the element. The support element may comprise an upper surface, and the recess may comprise an upper opening provided in the upper surface of the support element. The recess may comprise a base or bottom surface which supports the tissue construct, and the support element may define the base of the recess.

It will be understood that references to the 'top' and 'bottom' of the tissue construct support element, and indeed to 'upper' and 'lower' surfaces of the support element, are to be considered during use, when the support element is located in the bioreactor.

The tissue construct support element may define at least part of a boundary of the space. The support element may comprise a wall defining the boundary, which may be a sidewall. The wall may define a closed-sided space, and so may define a complete perimeter of the space. The support element may comprise at least one aperture extending laterally through the wall. The wall may therefore define an at least partially open-sided space.

The tissue construct support element may be generally annular in shape, and so may be in the shape of a ring. The space may be generally circular in shape. In use, the support element may be arranged to surround the tissue construct. The space may be shaped to suit the desired shape of the tissue engineered construct which is to be formed. This may be dependent upon factors including the type of implant which the tissue engineered construct is to be used to form. The invention provides the possibility of forming a tissue construct having a bespoke (i.e. patient-specific) shape that is determined, for example, from a magnetic resonance imaging (MRI) scan of a joint where tissue damage has occurred and the tissue is to be repaired.

A gap or spacing may be provided between the tissue construct support element and the tissue construct. This may facilitate access to the tissue construct for materials such as a culture medium. The gap may be provided between a wall of the support element and the tissue construct, in particular between a sidewall of the support element and a sidewall or walls of the tissue construct. The gap may be dimensioned to accommodate an increase in dimension(s) of the tissue construct (particularly a width), occurring due to the deposition of tissue matrix.

The tissue construct support element may be provided integrally with the bioreactor. The tissue construct support element may be provided as a separate component which is mountable within the bioreactor. The bioreactor may comprise a well or chamber which receives the tissue construct support element and the tissue construct, and which is arranged so that the load applicator can apply the mechanical load to the support element and construct located within the well. The well may contain a culture medium, which may be a chondrogenic culture medium (where the tissue engineered construct is to form a cartilage implant), for stimulating the deposition by the cells of tissue matrix in the construct.

The load which is applied may be a substantially constant (i.e. substantially non-varying) magnitude load. Upon commencement of cyclical loading, the tissue construct support element may absorb/support a majority of the applied load. Whilst the tissue construct support element initially bears a majority of the load, the tissue construct is still compacted/compressed, and the resultant strain applied to the construct may be large enough to produce suitable stress in the residing tissue matrix and cells to trigger anabolic effects. As more tissue matrix is deposited, the construct becomes thicker and stiffer. The amount of strain applied to the construct therefore increases, as does the amount of stress applied (as the construct takes a greater proportion of the applied load from the bioreactor). This iterative process may continue in an effectively automatic process, until the tissue construct bears all (or substantially all) of the applied load.

The cyclical loading may be applied at a desired frequency, for a certain period of time each day, over a period comprising a plurality of days. By way of example, the loading may be applied: at a frequency of around 1 Hz; for a period of around 1 hour per day; and over a period of up to 84 days.

The mechanical load which is applied to the tissue construct may be of a magnitude which results in a strain of at least about 10%, optionally at least about 13%, in the construct. The mechanical load which is applied to the tissue construct may be of a magnitude which results in a strain of no more than about 30%, and optionally no more than about 23%. Strains in the range of about 13% to about 23% have been found to produce particularly good results in terms of stimulating the cells to deposit tissue matrix.

The load applicator may be mounted for movement towards and away from the tissue construct support element and tissue construct, to impart the load. The load applicator may be shaped so that it can at least initially contact both the tissue construct and the support element. The load applicator may be shaped so that it can contact at least part of an upper surface of the support element. The load applicator may have a head which is dimensioned so that it can at least initially contact both the tissue construct and the support element. The load applicator, in particular its head, may be dimensioned so that it covers the space defined by the support element.

It will be understood that the mechanical load is cyclical in that the load is applied in a procedure comprising a plurality of cycles of application and release of loading. The bioreactor may comprise an actuating arrangement for operating the load applicator, in particular for moving the load applicator towards and away from the tissue construct support element and the tissue construct. The cyclical mechanical load may be applied by a plunger, which may be mechanically, electro-mechanically, electrically or fluid operated. A pre-stressed load element, such as a spring, may be employed to urge the load applicator towards the construct/support element, to apply the mechanical load. The actuating arrangement may be arranged to move the load applicator away from the support element and tissue construct against a biasing force of the pre-stressed load element.

The scaffold may be of a non-woven material. The scaffold may be fibrous or filamentous. The scaffold may be a multi-filament material comprising a plurality of filaments, the filaments being entangled to form a scaffold having a porous, open structure. This may facilitate seeding of the scaffold, and may promote the passage of materials (e.g. culture medium) into the construct comprising the scaffold, and unhindered deposition of tissue matrix in the construct.

The filaments may be entangled by any suitable process, such as a mechanical process (e.g. needle-punching) or a hydraulic process (e.g. hydro-entanglement). The filaments may be monofilaments or multi-filament yarns. The material may be polymeric, and may be polyethylene terephthalate (PET), known commercially by numerous names amongst which are TERYLENE™, DACRON™ or TREVERA™.

The scaffold, in particular filaments of the scaffold, may be of chitosan, or collagen, alternatively of a gel material, which may be a hydrogel. The scaffold may be of a multi-pored material such as a foam, foamed material or sponge.

The scaffold may be of a material that is degradable or bioresorbable.

The tissue construct may comprise at least one fixation feature or anchoring element, which may serve for fixing or anchoring the tissue engineered construct to tissue in the body of a patient. The at least one anchoring element may be formed integrally with the scaffold. The at least one anchoring element may be a provided separately from the scaffold and secured to the scaffold. The at least one anchoring element may be secured by a mechanical process (e.g. needle-punching), a hydraulic process (e.g. hydro-entanglement), or by an adhesive. The at least one anchoring element may be elongate, and may comprise at least one monofilament, or multifilament yarn. The anchoring element may be formed into a loop. The anchoring element may be formed into a plurality of loops. The anchoring element may comprise at least one textile component, which may comprise a plurality of monofilaments or multifilament yarns. The textile component may be woven. The tissue construct may comprise a plurality of anchoring arms or legs extending from the scaffold, each arm/leg formed from or comprising at least one anchoring element.

The scaffold may be seeded with cells and the resulting construct cultured in culture medium for a certain period (typically of the order of a number of days) prior to being located in the bioreactor. Possible cell types which might be employed for seeding the scaffold include: chondrocytes, synoviocytes, mesenchymal stem cells, or any other cell type that has the potential to differentiate into the desired phenotype. The cell seeded scaffold may be placed in a static culture in a chondrogenic medium for a period of around four weeks.

According to a third aspect of the present invention, there is provided an implantable tissue engineered construct having an elastic modulus of at least 8 MPa.

The tissue engineered construct may comprise a scaffold which has been seeded with cells to produce a tissue construct, the construct subjected to a tissue engineering method, in particular the method of the first aspect of the present invention, to stimulate the deposition of tissue matrix in the scaffold and produce the tissue engineered construct. The tissue engineered construct may form an implant suitable for implantation in the human or animal body.

Natural human cartilage tends to have varying elastic moduli, typically in the range of 1 to 18 MPa, depending upon the region of bone over which the cartilage lies. Ultimately this is dependent upon the loading which the cartilage experiences during use. For example, in knee cartilage, the portions of cartilage overlying the femoral bone condyles tend to experience higher loading than the portion overlying the trochlea. Consequently, the portions of cartilage overlying the femoral bone condyles typically have moduli of elasticity in the region of 8 to 18 MPa, compared to around 1 to 4 MPa for the portion overlying the trochlea.

As discussed above, it is believed that constructs with mechanical properties comparable to those of native cartilage would be more likely to survive the rigors of the mechanical environment within the knee joint, to integrate with the surrounding native cartilage, and to produce long term repair. None of the prior tissue engineering techniques developed to date has been able to produce a tissue engineered construct having sufficiently high moduli of elasticity to meet these requirements. In particular, none of the techniques have enabled the production of a tissue engineered construct having sufficiently high modulus of elasticity to form a successful cartilage implant. A significant threshold modulus for a tissue engineered construct which is to form a cartilage implant (particularly knee cartilage) is 8 MPa, being the typical lower threshold modulus of natural cartilage in the higher loading zones of the knee joint.

The method and bioreactor of the first and second aspects of the present invention provide the ability to form a tissue engineered construct having a modulus of elasticity of at least about 8 MPa, which is suitable for forming a cartilage implant. Whilst the present invention has a particular application in the formation of a cartilage implant such as a knee cartilage implant, it is not restricted to forming such implants, and could be applied to numerous other musculoskeletal tissues including, but not restricted to, meniscus and fibrocartilage such as the annulus fibrosus of intervertebral discs. It may also have an application in the formation of a bone implant, with appropriate modifications of key features/parameters such as an elastic modulus of the support element, to account for the significantly greater modulus that bone tissue will have compared e.g. to cartilage.

The implantable tissue engineered construct may have an elastic modulus of up to about 20 MPa, optionally up to about 30 MPa. Moduli of elasticity at these higher levels may be attainable following the method and using the bioreactor of the present invention.

Further features of the tissue engineered construct may be derived from the text set out above relating to the method/bioreactor of the first and/or second aspect of the invention.

According to a fourth aspect of the present invention, there is provided a method of repairing human or animal body tissue comprising:
 forming an implantable tissue engineered construct in a method comprising the steps of:
  seeding a scaffold with cells to form a tissue construct;
  locating the tissue construct in a space defined by a tissue construct support element;
  locating the tissue construct support element within a bioreactor; and
  operating a load applicator of the bioreactor to apply a cyclical compressive mechanical load to the tissue construct, to stimulate the deposition of tissue matrix in the tissue construct;
  in which the tissue construct, the tissue construct support element and the load applicator are arranged so that the load applicator can at least initially contact both the tissue construct and the tissue construct support element, so that at least part of a total load generated by the load applicator is borne by the tissue construct support element;
 and subsequently implanting the tissue engineered construct in the body of a patient.

The method may comprise the further steps of:
 determining a location of an area of body tissue where the construct is to be implanted;
 assessing a shape of a portion of the tissue to be removed from said location; and forming the construct with a shape which is appropriate for implantation at said location following removal said portion of the tissue.

The shape of the portion of tissue to be removed may be determined using a suitable technique, such as a magnetic resonance imaging (MRI) technique. A plurality of constructs may be implanted at said location. The method may comprise selecting a tissue construct support element defining a space which is appropriate to the shape of the construct which it is desired to form for implantation at said location.

Further features of the method of the fourth aspect of the invention may be derived from the text set out above relating to the any one of the first to third aspects of the invention.

According to a fifth aspect of the present invention, there is provided a method of repairing human or animal body tissue comprising implanting an implantable tissue engineered construct having an elastic modulus of at least 8 MPa.

Further features of the method of the fifth aspect of the invention may be derived from the text set out above relating to any one of the first to fourth aspects of the invention.

Reference is made herein to the following terms which, in the context of the present invention, may be understood to have the following meanings:

Tissue engineered construct—this is a tissue construct, i.e. a scaffold which has been seeded with cells, which has been subjected to a tissue engineering procedure to promote the deposition of tissue matrix in the construct.

Tissue matrix—this is the tissue which is deposited in the tissue construct by the cells which have been seeded in the scaffold.

Scaffold—this is an artificial structure capable of supporting three-dimensional tissue formation.

Seeding of cells—this is the process of populating the artificial scaffold structure with cells.

Bioreactor—this is a manufactured or engineered apparatus/device which supports a biologically active environment.

BRIEF DESCRIPTION OF THE DRAWINGS

Embodiments of the present invention will now be described, by way of example only, with reference to the accompanying drawings, in which:

FIG. 9 is a plan view of the tissue construct shown in FIG. 8;

FIG. 9A is a cross-sectional side view of a tissue construct which is a variation of that shown in FIG. 9, taken about line A-A;

FIG. 10 is a plan view of another alternative tissue construct;

DETAILED DESCRIPTION OF THE DRAWINGS

Figure 1:
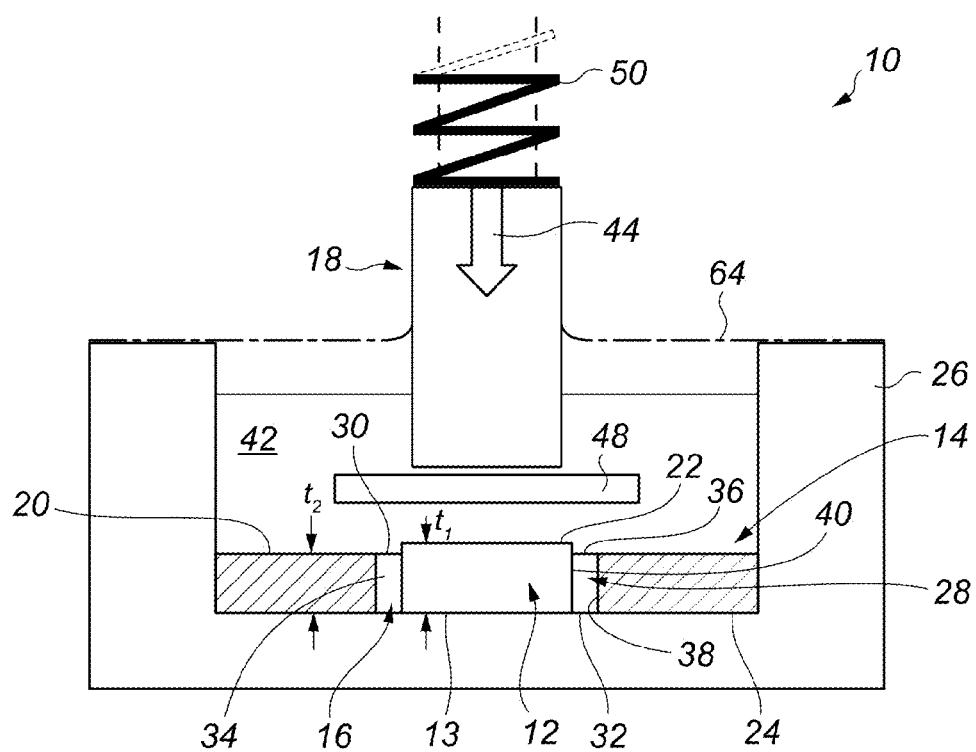
FIG. 1 is a schematic cross-sectional front view of part of a bioreactor, showing steps in a method of forming an implantable tissue engineered construct, according to an embodiment of the present invention.

Turning firstly to FIG. 1, there is shown a schematic cross-sectional front view of part of a bioreactor, showing steps in a method of forming an implantable tissue engineered construct, according to an embodiment of the present invention. The bioreactor is indicated generally by reference numeral 10. The method generally comprises the following steps. A tissue construct 12 is formed by seeding a suitable scaffold 13 with cells. Typically the cells will be autogenous cells, taken from a patient, but may be allogenic cells taken from a suitable donor. If the construct was de-cellularised, then xenogeneic cells from a suitable donor animal could also be used. A tissue construct support element 14 is located within the bioreactor 10, and defines a space 16 within which the tissue construct 12 is located. The bioreactor 10 comprises a load applicator 18 which can be operated to apply a cyclical compressive mechanical load to the tissue construct 12, to stimulate the deposition of tissue matrix in the construct, by the cells which have been seeded in the scaffold 13. The tissue construct 12, support element 14 and load applicator 18 are arranged so that the load applicator can at least initially contact both the construct 12 and the support element 14. In this way, at least part of a total load generated by the load applicator is borne by the support element 14. Accordingly, the construct 12 is not initially subjected to unduly high strains (and so high resultant stresses) which could damage tissue deposited in the construct scaffold, and impair the deposition of further tissue matrix. However, sufficient strain is applied to the construct 12 to stimulate the deposition of tissue matrix.

The method of the present invention facilitates the creation of tissue engineered constructs in-vitro, by the use of cyclic compressive loading that effectively adapts based on the continually developing physical and mechanical properties of the construct itself. Specifically, as the tissue construct 12 increases its thickness and modulus, and hence its stiffness (by the continual deposition of matrix by residing cells), the strain and stress applied to the construct increase accordingly. This is believed to provide continued suitable cellular stimulation throughout the culture within the bioreactor, to cause the constructs to reach desirable stiffness, and therefore be functional as a tissue replacement/implant.

Figure 2:
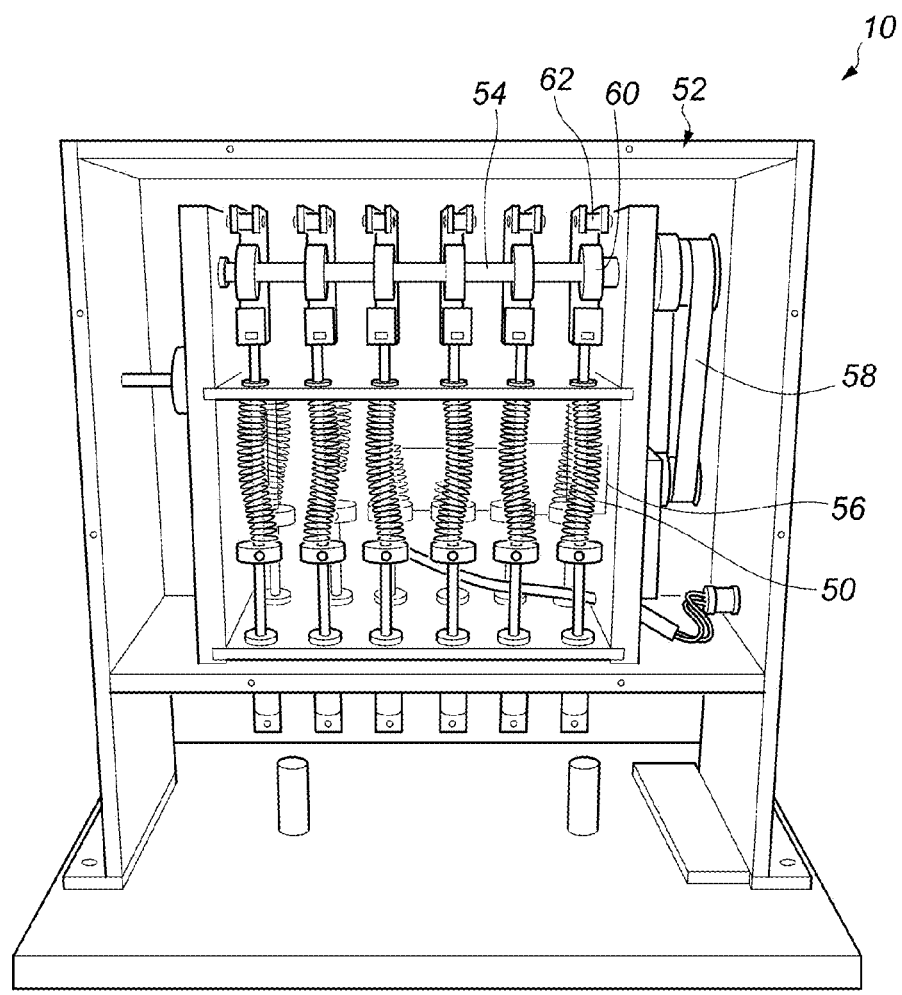
FIG. 2 is an enlarged perspective view of the bioreactor of FIG. 1, taken from the front.

FIG. 2 is an enlarged perspective view of the bioreactor 10, taken from the front. Referring again to FIG. 1, the scaffold 13 can be of any structure which is suitable for being seeded with cells. In the illustrated embodiment, the scaffold 13 takes the form of a pad comprising a plurality of filaments (typically monofilaments) which have been entangled by a suitable process, such as needle punching or hydro-entanglement. Suitable materials for the filaments include polymers, and in particular polyethylene terephthalate (PET). A material may be employed which is degradable or bioresorbable. Fibrous/filamentous scaffolds of this type are particularly suitable, but other materials including gels such as hydrogels, and multi-pored materials such as foams, foamed materials and sponges can be employed, as will readily be understood by persons skilled in the art.

The scaffold 13 is seeded with suitable cell types which can include chondrocytes, synoviocytes, mesenchymal stem cells or any that have the potential to differentiate into the desired phenotype. It will be understood that the cells which are seeded on to the construct 13 are selected according to the desired tissue implant which is to be formed. The constructs are then subjected to a pre-culture process (typically up to 4 weeks) in a culture medium, which stimulates the deposition of tissue matrix in the scaffold 13, to form the tissue construct 12 which is to undergo the method of the present invention. One example of a suitable pre-culture process will be discussed below. However, the skilled person will be aware suitable processes that can be employed.

The support element 14 is of a material having an elastic modulus which is greater than an elastic modulus of the tissue construct 12, following completion of the pre-culturing procedure and prior to the commencement of load application. The material which is selected to form the support element 14 is, in a preferred embodiment, resiliently deformable and capable of initially resiliently supporting the majority of the compressive mechanical loading intended to be used for a construct of a certain surface area (the larger the construct area, the larger being the load required to generate a stress resulting in a desired strain). Typical materials will have a compressive elastic modulus of at least around 2 MPa, optionally at least around 2.5 MPa, and optionally around 2.64 MPa. However, in general terms, materials having a modulus of around 2 MPa to around 5 MPa may be employed. Materials having such a modulus of elasticity are relatively compressible, and may be particularly suited for forming the support element 14. Suitable materials include biocompatible polymeric materials, and in particular silicone materials such as the commercially available Sylgard 184 elastomer, VWR International, Lutterworth, UK, 634165S. The support element 14 formed from this material has a compressive modulus of around 2.64 MPa. In contrast, following completion of the culturing procedure, the tissue construct 12 typically has an elastic modulus of less than 0.5 MPa, and in particular around 0.2 MPa.

The tissue construct 12 is located in the space 16 so that it protrudes beyond an upper surface (or upper extent) 20 of the support element. As can be seen from FIG. 1, the construct 12 has an upper surface 22, which is located above the upper surface 20 of the support element 14. In the illustrated embodiment, the construct 12 and the support element 14 both sit on a base 24 of a well 26 of the bioreactor 10, and the construct 12 is arranged to protrude beyond the upper surface 20 of the support element 14 because it has a greater mean thickness ($t_1$) of its cross-section than a corresponding mean thickness ($t_2$) of the support element 14. A ratio of t1/t2 is suitably between 1.1 and 1.2, so that the load applied would initially compress the construct 12 resulting in a strain between about 15% and about 25%. Taking account of the relative initial modulus of the construct 12 and the modulus of the support element 14 mentioned above, this would result in the support element experiencing a strain of about 3-5%. The tissue construct 12 typically has a thickness ($t_1$) of between 1.11 mm and 1.25 mm, and the support element 14 a thickness ($t_2$) of approximately 1 mm. For thicker cartilage repairs the construct 12 and support element 14 thicknesses are adjusted accordingly.

The support element 14 comprises an aperture 28 which extends through the support element 14, and which defines the space 16. The aperture comprises an upper opening 30, a lower opening 32, and a passage 34 which extends between the upper and lower openings. In this way, the construct 12 can be located within the space 16 and can rest upon the base 24 of the well 26. The support element 14 is generally annular in shape, and the space 16 is generally circular in shape in plan view. However, the support element 14 and the space 16 may be of any suitable, desired shape.

The construct 12 and support element 14 are shaped so that a gap 36 is defined between the construct and the support element, in particular between a side wall 38 of the support element and a side wall or walls 40 of the construct. The gap 36 facilitates access to the construct 12 for materials such as a culture medium 42 contained within the well 26, and also accommodates any increase in width of the construct 12 which occurs during the deposition of tissue matrix. Indeed, it will be understood that a width of the construct 12 may increase during performance of the method of the present invention, at least partly occupying the gap 36. Accordingly, the space 16 defined by the support element 14 may serve to define the final shape of the tissue engineered construct 12. The shape of the space 16 may therefore be chosen to form a tissue engineered construct 12 of desired shape/dimensions.

The support element 14 defines at least part of a boundary of the space. In the illustrated embodiment, the wall 38 of the support element 14 defines the boundary, and defines a closed-sided space 16. The wall 38 thereby defines a complete perimeter of the space 16.

In the illustrated embodiment, the support element 14 is shown as a separate component which can be positioned within the bioreactor well 26. However, it will be understood that, in an alternative embodiment, the support element may be provided integrally with the well 26. This may particularly be the case if a material is selected for the support element 14 which is the same or similar to that of the well 26, so that the well can be formed with an integral support element.

The mechanical load which is imparted on the construct 12 and, during at least part of the process, the support element 14, is a compressive mechanical load, the direction of loading indicated by the arrow 44 in FIG. 1. The difference in elastic modulus of the construct 12 compared to the support element 14 at commencement of the procedure is such that the support element 14 initially bears a majority of the applied load. However, whilst the support element 14 initially bears a majority of the load, the construct 12 is still compacted, and the resultant strain applied to the construct is selected to be large enough to produce suitable stress in the residing tissue matrix and cells to trigger anabolic effects.

Figure 3:
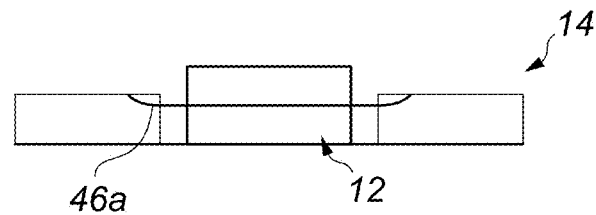
FIGS. 3 to 6 are schematic illustrations of a tissue construct and a tissue construct support element employed in the bioreactor and method of FIGS. 1 and 2, the construct and support element shown at various stages in the method and illustrating the loading in the support element.
Figure 4:
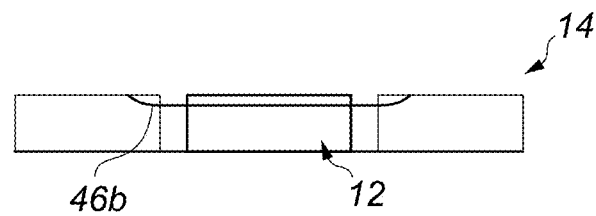
Figure 5:
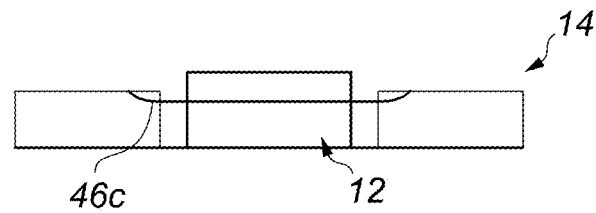
Figure 6:
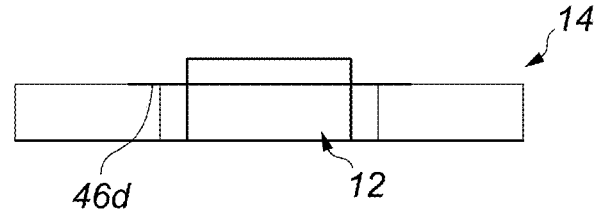

As more tissue matrix is deposited, the construct 12 becomes thicker and stiffer. The amount of strain applied to the construct 12 therefore increases, as does the amount of stress applied (as the construct takes a greater proportion of the applied load). This is shown in the schematic views of FIGS. 3 to 6, which illustrate the tissue construct 12 and support element 14 at various stages in the method. FIG. 3 shows the construct 12 at day zero, i.e. commencement of the procedure (and so immediately following four weeks pre-culture). The broken line 46a indicates the typical extent to which the support element 14 is deformed by the load applicator 18 at commencement of the procedure, when the construct 12 has a low elastic modulus. FIG. 4 shows the construct 12 after 28 days, FIG. 5 after 56 days, and FIG. 6 after 84 days, the relative deformation of the support element 14 being indicated respectively by the broken lines 46b, c and d. As can be seen, as the tissue construct 12 becomes thicker and stiffer so that the extent of deformation of the support element 14 becomes smaller over time. This is because a greater proportion of the load applied by the applicator 18 is supported by the construct 12. Indeed, at day 84, a majority or all of the applied load is supported by the construct 12, so that the support element 14 is not deformed, or is only deformed to a very limited extent.

The cyclical loading is applied at a desired frequency, for a certain period of time each day and over a period comprising a plurality of days. In the illustrated embodiment, loading is applied over an 84 day period, at a frequency of around 1 Hz, for a period of around one hour per day. In other words, the load is imparted on the construct 12/support element 14 in a procedure comprising a plurality of cycles of application and release of load having a frequency of 1 Hz, i.e. once per second. The load applied remains constant throughout the procedure, and in the illustrated embodiment a relatively high force (in the context of prior procedures, and for a construct of certain surface area) of 5 N is applied. The load is sufficient to result in a compressive strain in the tissue construct 12 of at least about 13% (upon commencement of loading after pre-culture period), which has been found to be advantageous in stimulating the deposition of tissue matrix in the scaffold 13. Application of sufficient load to impart a strain in the range of about 13% to about 23%, and typically no more than about 30%, has been found to be suitable.

The load applicator 18 is mounted for reciprocating movement towards and away from the construct 12 and support element 14, to impart the load. The applicator 18 is shaped so that it can at least initially contact both the construct 12 and the support element 14. In this way, part of the load generated by the load applicator 18 is borne by the support element 14. The applicator 18 takes the form of a plunger, and has a head 48 which is dimensioned to provide the required contact. The plunger head 48 typically completely covers and overlaps boundaries of the space 16 defined by the support element 14.

The applicator 18 can be driven in any suitable fashion to impart the mechanical load, including mechanically, electro-mechanically, electrically and fluid operated. However, in the illustrated embodiment, the applicator 18 is biased by a pre-stressed load element in the form of a compression spring 50, which urges the applicator towards the construct 12/support element 14.

As best seen in FIG. 2, the bioreactor 10 comprises an actuating arrangement 52 for moving the applicator 18 away from the construct 12 and support element 14, against a biasing force of the spring 50. Advantageously, this ensures that a consistent total load is applied, by means of the pre-stressed compression spring 50. The actuating arrangement comprises a shaft 54 which is driven (and so rotated) by a motor 56, via a drive belt 58. The shaft 54 carries a cam 60, which cooperates with a cam surface on a cam element 62 coupled to the plunger 18. As the shaft 54 is rotated by the motor 56, the cam 60 acts on the cam element 62, to raise the head 48 of the plunger 18 away from the construct 12 and support element 14, against the force of the spring 50 (to release the load). As shown in FIG. 2, the bioreactor 10 comprises a plurality of plungers 18, each of which is associated with a respective well 26 that contains a construct 12 and support element 14. Each plunger 18 has its own associated cam 60, which is driven by the shaft 54. In this way, a plurality of constructs 12 can be loaded simultaneously.

As mentioned above, the support element 14 is positioned within the well 26, and the construct 12 located within the space 16. A suitable culture medium is supplied in the well 26 which, where the tissue engineered construct is to form a cartilage implant, is a suitable chondrogenic culture medium. The well 26 is sealed using a suitable sealing film 64, such as the commercially available flexible polyurethane film OpSite Flexigrid, Smith & Nephew, Hull, UK, 4631. The film 64 seals around the plunger 18 and to the well 26, to provide a sterile environment for culturing the construct 12. The film 64 can maintain a seal around the plunger 18 during movement to apply the load.

Results of tests on tissue constructs 12 formed employing the above procedure have demonstrated that it is possible to produce constructs with moduli of elasticity significantly greater than 8 MPa, and typically with moduli up to around 19 MPa, although it is believed that moduli of up to around 30 MPa are attainable. Tissue engineered constructs having moduli of elasticity of at least about 8 MPa are particularly suitable for forming a cartilage implant. It is generally accepted in the relevant literature that loading on natural cartilage tissue, for example in the human knee joint, can be in the region of 7.1 (±1.9) MPa (mean±standard deviation) in zones of higher loading. The constructs which are engineered according to the above method are thus significantly stiffer than those produced following prior techniques. This has the further advantages that the implant formed is more likely to survive the rigours of the mechanical environment within the knee joint, to integrate with the surrounding native cartilage, and to provide an effective long term repair.

Figure 7:
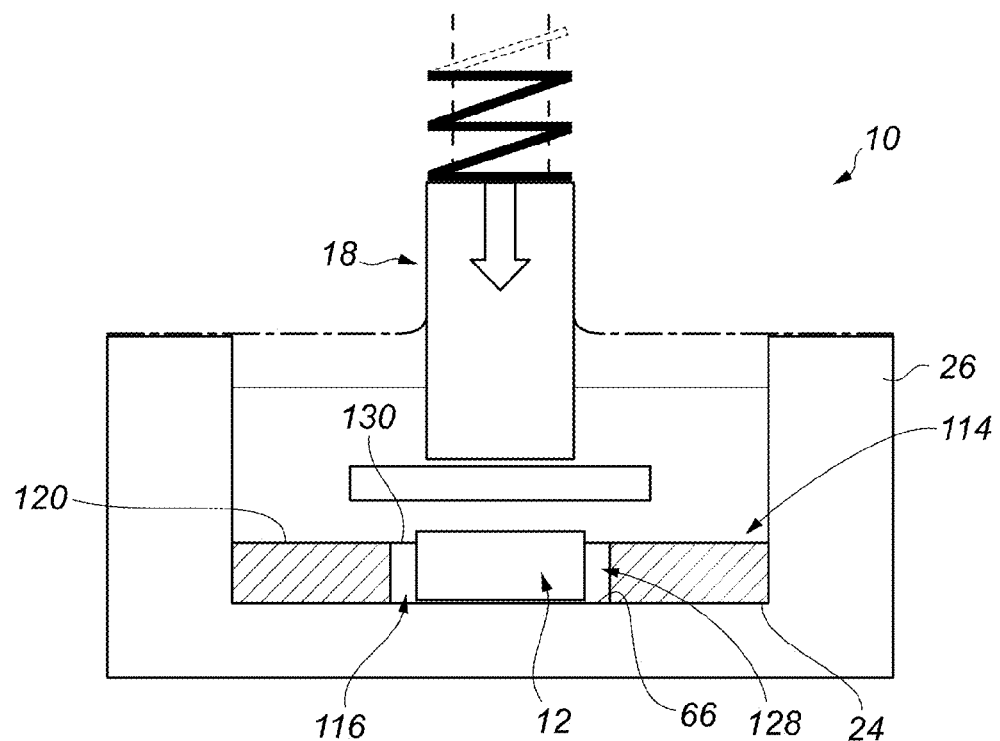
FIG. 7 is a view of the part of the bioreactor of FIG. 1, showing steps in a method of forming an implantable tissue engineered construct employing an alternative tissue construct support element.

Turning now to FIG. 7, there is shown a view of the bioreactor 10 of FIG. 1 illustrating steps in a method of forming an implantable tissue engineered construct employing an alternative tissue construct support element 114. Like components of the support element 114 with the support element 14 shown in FIGS. 1 to 6 share the same reference numerals, incremented by 100.

In this embodiment, the support element 114 comprises a recess 128 which extends part-way through the support element, and which defines a space 116 which receives the tissue construct 12. The recess 128 comprises an upper opening 130, provided in an upper surface 120 of the support element 114, and has a base or bottom surface 66 which supports the construct 12. The support element 14 rests on the base 24 of the bioreactor well 26, and the construct 12 sits on the base 66 of the recess 130. The construct 12 protrudes from the space 116 in a similar way to the construct shown in FIG. 1, and the method and bioreactor 10 otherwise functions as described above.

Figure 8:
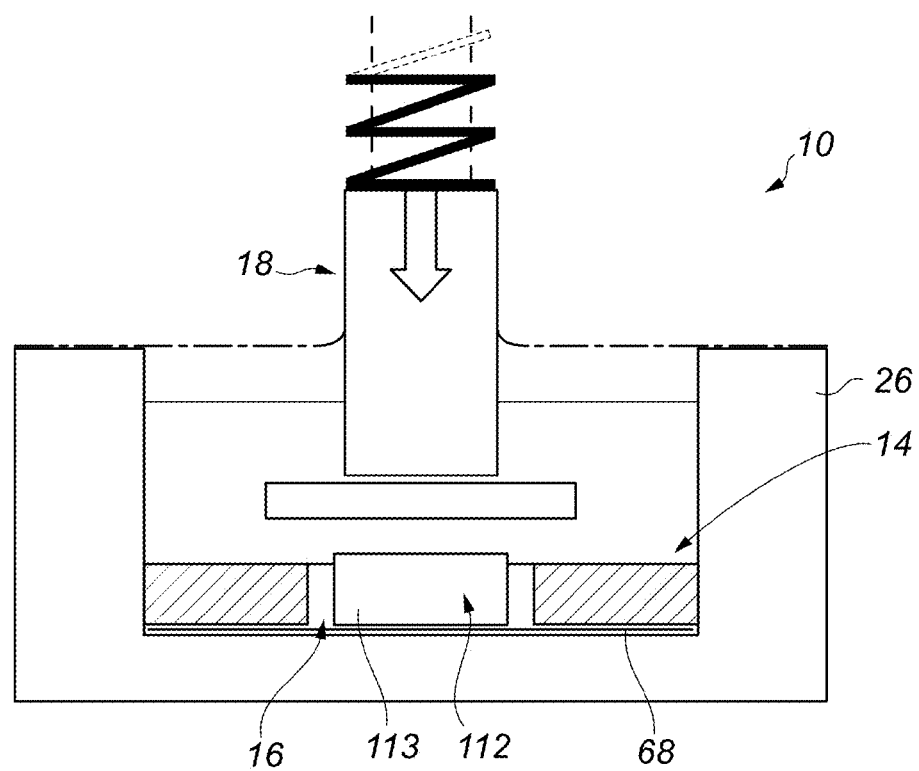
FIG. 8 is a view of the part of the bioreactor of FIG. 1, showing steps in a method of forming an implantable tissue engineered construct employing an alternative tissue construct.

Turning now to FIG. 8, there is shown a view of the bioreactor 10 of FIG. 1 illustrating steps in a method of forming an implantable tissue engineered construct employing an alternative tissue construct 112. Like components of the construct 112 with the construct 12 of FIGS. 1 to 7 share the same reference numerals, incremented by 100.

In this embodiment, the tissue construct 112 comprises at least one fixation feature or anchoring element 68, which serves for fixing or anchoring the tissue engineered construct 112 to tissue in the body of a patient. In the illustrated embodiment, the construct 12 comprises a plurality of anchoring elements 68, as can best be seen in the plan view of FIG. 9. Typically, the anchoring elements 68 are provided separately from a scaffold 113 of the tissue construct, and are secured to the scaffold by a suitable procedure. However, the anchoring elements 68 may be formed integrally with the scaffold 113.

In the illustrated embodiment, the anchoring elements 68 are formed from a monofilament, or a multifilament yarn 69, which is secured to the scaffold 113 by a mechanical or hydraulic process. In particular and as described above, the scaffold 113 typically takes the form of a filamentous open scaffold, such as of a needle punched material. The monofilament or yarn 69 forming the anchoring elements 68 can be secured by a mechanical process of needle punching, or a hydraulic process of hydro-entanglement. In a variation, an adhesive may be employed.

Following the teachings of International patent publication number WO-2013/017835 assigned to Xiros Limited, the disclosure of which is incorporated herein by way of reference, at least some of the anchoring elements 68 take the form of elongate loops which extend from the scaffold 113. The anchoring elements are formed into a first set of elongate loops 68a, 68b and a second set of elongate loops 68c, 68d. The first set of loops 68a, b are formed using the monofilament or yarn 69, which passes around pins (not shown) positioned in locations where eyelets 70 of the loops 68a, b are to be formed. The monofilament or yarn 69 passes back and forth between the successive pins to form the array of loops 68a, b.

In a similar fashion, a separate monofilament or yarn 71 is used to form the loops 68c, d. The monofilament or yarn 71 passes back and forth around a separate set of pins (not shown), the loops 68c, d being arrayed perpendicularly to the loops 68a, b. The scaffold 113 is laid over the arrays of loops 68a to d, and then secured using one of the methods described above.

If desired, the scaffold 113 may comprise two separate scaffold pads 113a and 113b, as shown in the sectional view of FIG. 9A. The yarns 69 are formed into the array of loops 68a to d over the first pad 113a, as shown in FIG. 9A, the second pad 113b is then laid over the loops, and the composite is needle punched or hydro-entangled to form the finished scaffold.

FIG. 10 is a plan view of a tissue construct in accordance with another embodiment of the present invention, and which is a variation on the embodiment shown in FIG. 9. Like components with the construct 12 of FIGS. 1 to 7 share the same reference numerals, incremented by 200. In this embodiment, a single monofilament or multifilament yarn 269 is used to form a plurality of generally radially arranged loops 268. The drawing shows first and second ends 72 and 74 of the monofilament or yarn 269, and illustrates (in broken outline) a pattern which is followed to form the various loops 268. Construction of the tissue construct 212 is otherwise as described above in FIG. 9, or optionally in FIG. 9A.

Figure 11:
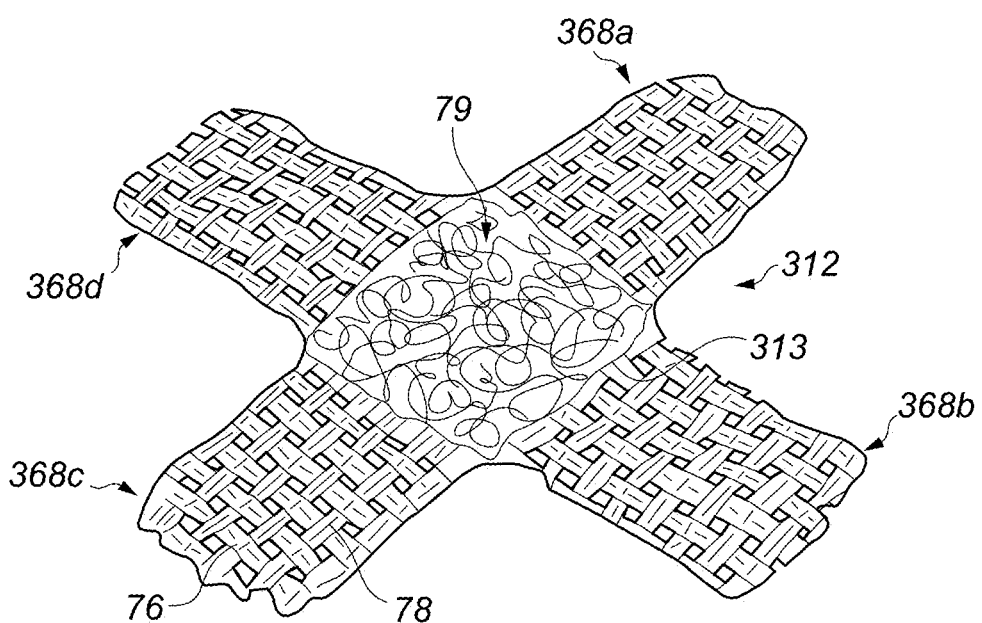
FIG. 11 is a perspective view of another alternative tissue construct.

FIG. 11 is a perspective view of a further alternative tissue construct, indicated generally by reference numeral 312. In this embodiment, a scaffold 313 comprises anchoring elements in the form of arms or legs 368a to d which are textile elements, typically having a woven structure comprising warps 76 and wefts 78. The anchoring legs 368a to d are legs of a generally cross-shaped structure which is woven as a single component and then secure to the scaffold 313, which is again of a multifilament structure of the type described above. FIG. 11 illustrates fibres 79 used to form the scaffold 313 which, as discussed above, may be monofilaments or yarns. Any of the methods described above in relation to the previous embodiments may be employed to secure the textile structure to the scaffold.

Figure 12:
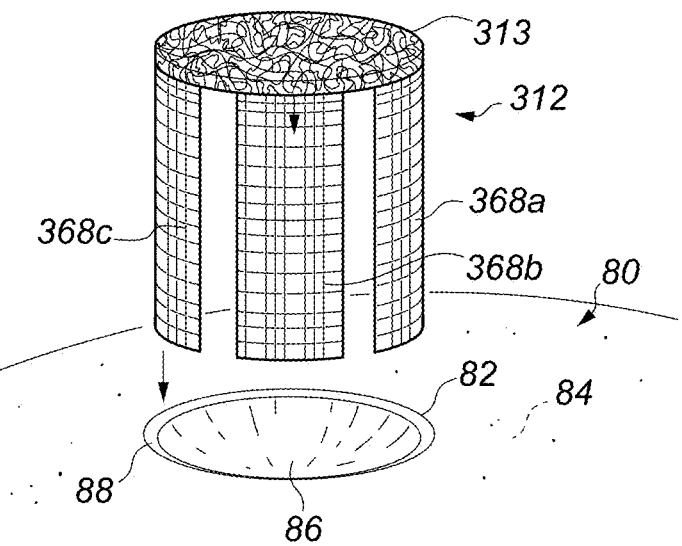
FIG. 12 is a perspective view of the tissue construct of FIG. 11 shown following completion of the steps involved in the method of forming the construct, illustrating steps in a method of repairing human or animal body tissue employing the construct.

FIG. 12 shows a method of implantation of the tissue construct 312, following completion of the culturing procedure described above. Whilst the method is described with specific reference to the tissue construct 312, the method may equally be employed to anchor any of the constructs 112 or 212 shown and described in FIGS. 8 to 10 above. In addition, it will be understood that aspects of the method of implantation described herein will apply equally to the other tissue constructs disclosed herein and which do not incorporate anchoring elements.

FIG. 12 shows a bone 80, typically the surface of a femoral bone of a knee joint, which has been prepared to receive a cartilage implant comprising the cultured tissue engineered construct 312. Native cartilage 82 residing on a surface 84 of the femoral bone 80 has experienced trauma, or has suffered a degenerative condition, in a region 86. A surgical procedure has been carried out to remove the cartilage 82 in the region 86, and an annular recess 88 has been cut in the femoral bone 80. The prepared tissue engineered construct 312 is positioned adjacent the region 86 where the native cartilage 82 has been removed, and the anchoring legs 368a to d are folded down and pushed in to the recess 88, using a suitable tool. The recess 88 has a depth which is sufficient to receive the anchoring legs 368a to d, which it will be understood may bunch up within the recess. The tissue construct scaffold 313, in which the tissue matrix has been cultured, is brought into contact with the bone surface 84 in the region 86, where the native cartilage 82 has been removed. The tissue engineered construct 312 therefore forms a cartilage implant which replicates the function of the native cartilage 82 in the damaged region 86.

In the method of implantation, a location of an area of body tissue where the construct 12 is to be implanted may be determined using a suitable technique, such as a magnetic resonance imaging (MRI) technique. A shape of a portion of the tissue to be removed from said location may be assessed, and the construct 12 may be formed with a shape which is appropriate for implantation at said location following removal said portion of the tissue. A plurality of constructs may be implanted at said location, which may have one of a standard or selected number of shapes (e.g. circular, square, rectangular, triangular, elliptical) and/or dimensions. The method involve selecting a tissue construct support element 14 defining a space 16 which is appropriate to the shape of the construct 12 which it is desired to form for implantation at said location.

An example and corresponding test results performed employing the method and bioreactor of the present invention will now be described in more detail.

Synoviocytes (obtained from the synovia of 6-month-old bovine metatarsophalangeal joints) were dynamically seeded onto polyethylene terephthalate (PET) scaffolds, up to a maximum of 250,000 cells per scaffold. The scaffolds comprised of non-woven 20 µm diameter filaments that had been plasma treated (Xiros Plc, Leeds, UK). Scaffolds had an overall porosity of 90.2% by volume and were in form of disks of 5 mm diameter and 0.9 mm thickness. Each cell seeded scaffold was cultured in 1 mL of chondrogenic medium, which consisted of Dulbecco's Modified Eagle's Medium/Ham's F12 medium (Invitrogen, Paisley, UK, 21041) supplemented with 10 ng/mL TGF-β3 (Invitrogen, Paisley, UK, PHG9305), $10^{-7}$ M dexamethasone, 1× Insulin-Transferrin-Selenium (Invitrogen, Paisley, UK, 51300044), 50 μg/mL L-ascorbic acid-2-phosphate sesquimagnesium salt hydrate (Sigma Aldrich, Gillingham, UK, A8960), 1% 100× antibiotic (AB) (Sigma Aldrich, Gillingham, UK, P0781) and 2 mM L-glutamine, and cultured at 37° C., 5% $CO_2$ and greater than 90% humidity. Cultures remained under these conditions for a total of 4 weeks to allow cellular matrix to be deposited. Medium was replaced every 3 to 4 days. The thickness of the resulting immature constructs was measured and those what were between 1110 and 1250 μm were selected for further culture. Each selected construct 12 was placed in the bioreactor 10, as shown in FIG. 1. The support element 14 was 1 mm thick and internal diameter 6 mm, and compressive modulus of 2.64 MPa (produced from Sylgard 184 elastomer, VWR International, Lutterworth, UK, 634165S). The plunger head 48 had a diameter of 8 mm Force applied was 5 N. From this configuration of the bioreactor 10, this caused initial strains between 13 and 23%. The constructs were subjected to 1 Hz cyclic compression for 1 hour per day, 5 days per week for either 28, 56 or 84 days. Medium was exchanged every 3 to 4 days.

Figure 13:
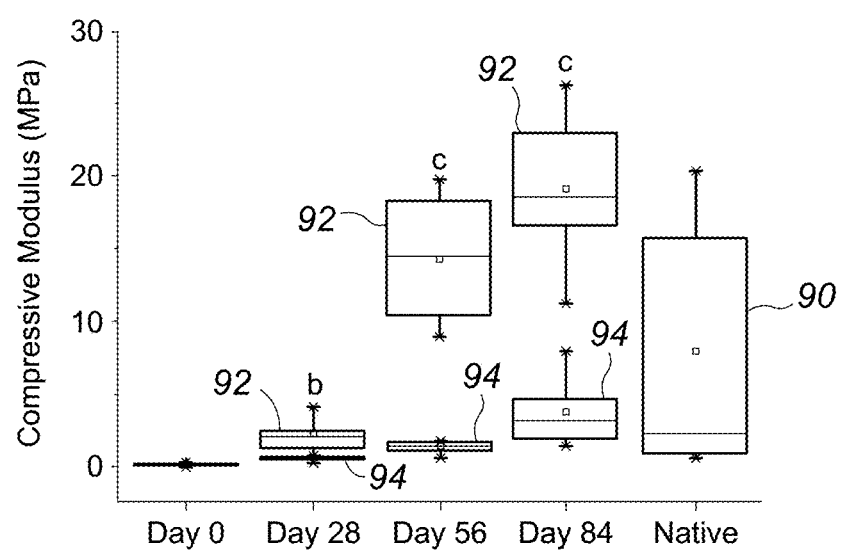
FIG. 13 is a graph showing the resulting moduli of exemplary loaded constructs (and experimental control, non-loaded constructs)

The resulting moduli of the loaded constructs (and experimental control, non-loaded constructs) are shown in FIG. 13. Compressive moduli measured at 18% strain of native bovine trochlear cartilage (indicated by numeral 90) and synoviocyte/PET constructs under 1 Hz 20% cyclic strain following pre-culture in chondrogenic medium for 4 weeks (Day 0) and then subjected to a mechanical loading regime for either 28, 56 or 84 days are shown. Moduli of loaded constructs (indicated by numeral 92) were greater than non-loaded constructs (indicated by numeral 94) throughout, substantially so at Day 56 and 84 (n=6-8). ≡b<0.001, *≡c<0.01. The moduli of the non-loaded constructs increased steadily at each time point, from a mean of 0.15 MPa at Day 0 (i.e. at the end of the 4-week pre-culture period) to an average of 3.6 MPa at Day 84. Moduli of loaded constructs increased significantly at Day 28 and Day 56 (mean of 2.2 MPa and 14.3 MPa respectively) compared with the previous time point. Although the modulus of loaded constructs continued to increase in the period between Day 56 (14.3 MPa) and Day 84 (19.0 MPa), this increase was not statistically significant (p=0.197). Thus the greatest effect of compressive mechanical loading on construct compressive moduli occurred between Day 28 and 56. Native bovine articular cartilage from the trochlea of the knee had an average modulus of 7.8 MPa (ranging from 0.5 MPa to 20.2 MPa).

Figure 14:
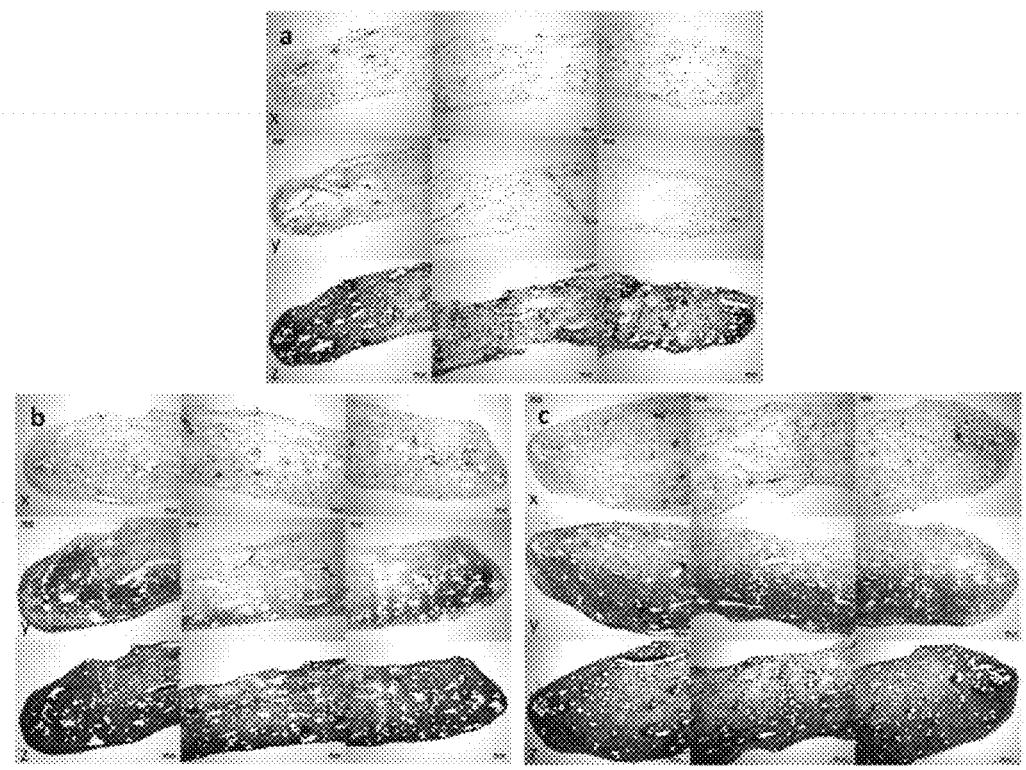
FIG. 14 represents histological appearance of sections from the exemplary constructs at (a) Day 0, (b) non-loaded Day 28 and (c) loaded Day 28 of culture with the presence of mechanical loading.
Figure 15:
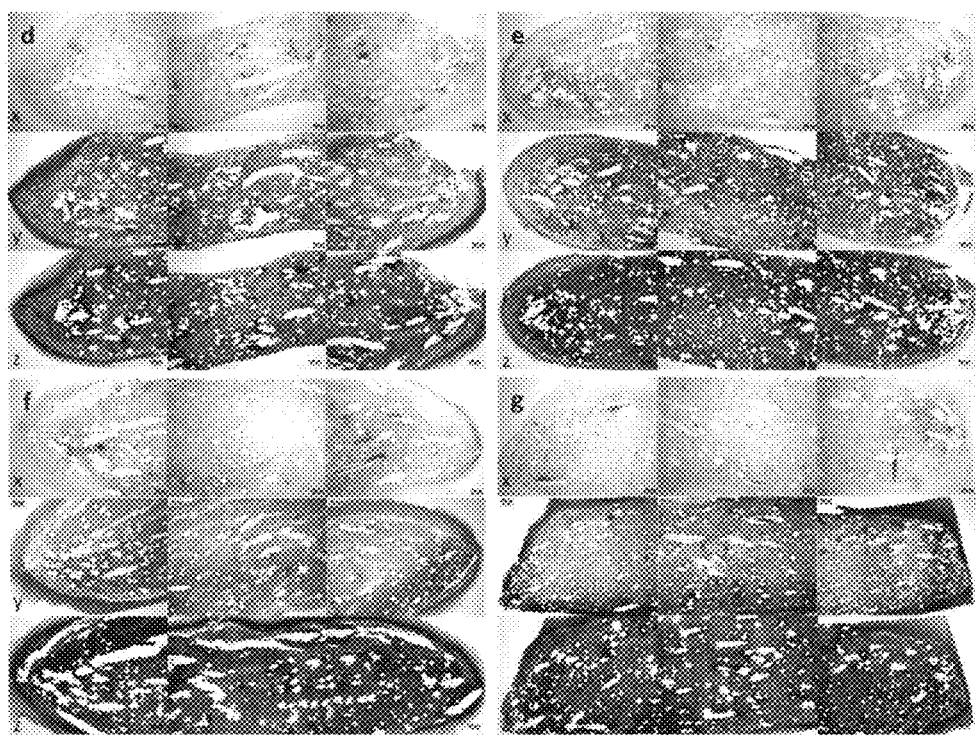
FIG. 15 represents histological appearance of sections from constructs at (d) non-loaded Day 56, (e) loaded Day 56, (f) non-loaded Day 84 and (g) loaded Day 84 of culture with the presence of mechanical loading.

The histological appearance of the constructs in the presence or absence of loading and at different time points in the culture period is shown in FIG. 14 and FIG. 15. FIG. 14 represents histological appearance of sections from constructs at (a) Day 0, (b) non-loaded Day 28 and (c) loaded Day 28 of culture with the presence of mechanical loading. Sections stained with x) antibodies to collagen type I, y) antibodies to collagen type II and z) Alcian blue/Sirius red. Three images, taken from the midpoint and each end of the construct are shown in each case, representing almost the entire construct. The scale bar is 200 μm. FIG. 15 represents histological appearance of sections from constructs at (d) non-loaded Day 56, (e) loaded Day 56, (f) non-loaded Day 84 and (g) loaded Day 84 of culture with the presence of mechanical loading. Sections stained with x) antibodies to collagen type I, y) antibodies to collagen type II and z) Alcian blue/Sirius red. Three images, taken from the midpoint and each end of the construct are shown in each case, representing almost the entire construct. The scale bar is 200 μm.

At Day 0 of the mechanical loading (after 4 weeks of pre-culture), low level staining was seen for collagen type I, collagen type II and Alcian blue (FIG. 14A), primarily localised at the periphery of the constructs' cross-sections.

By Day 28, there was a considerable increase in staining for collagen type II and Alcian blue in both loaded and non-loaded constructs (compared with Day 0), suggesting the deposition of a cartilage-like matrix. The laying down of cartilage-like matrix appeared to first occur at the edges of the construct and at either the top or bottom face of the construct (it was not possible to know which way up the constructs had been positioned in the bioreactor after they had been processed) (FIG. 14B and FIG. 14C). There was an increased amount of collagen type I staining throughout all constructs compared with Day 0. By Day 56, there was further increase in staining for collagen type II and Alcian blue in both loaded and non-loaded constructs accompanied by increased construct thickness, in comparison to Day 28. In addition, at Day 56 there were visible differences in histological appearance between loaded and non-loaded constructs. Homogeneity of staining for collagen type II and Alcian blue throughout the construct volume was different according to whether the constructs had been loaded or not. Loaded constructs (FIG. 15E) had greater homogeneity of staining than non-loaded constructs (FIG. 15D). In addition, loaded constructs had a more uniform shape compared with non-loaded constructs.

At Day 84, the histological appearance of the constructs was similar to that seen at Day 56, including the differences previously observed between loaded and non-loaded constructs. Non-loaded constructs had a variable cross-sectional shape and non-homogenous matrix staining for collagen type I, collagen type II and Alcian blue (FIG. 15F). Loaded constructs had uniform shape throughout their cross-section and homogenous matrix staining throughout (FIG. 15G).

These results display the maturation of the tissue engineered constructs to those that have compressive moduli values which are above 8 MPa and comparable to the higher range of native cartilage values, plus histological appearance comparable to native cartilage.

Various modifications may be made to the foregoing without departing from the spirit or scope of the present invention.

For example, whilst the tissue construct support element may define at least part of a boundary of the space, the support element comprising a wall defining the boundary (which may be a sidewall), the wall may comprise at least one aperture extending laterally through the wall. The wall may therefore define an at least partially open-sided space.

We claim:

1. A method of forming an implantable tissue engineered construct, the method comprising the steps of:
   providing a bioreactor comprising a well and a load applicator, the well having a base;
   locating a resiliently deformable tissue construct support element on the base of the well, the support element having an upper surface;
   seeding a scaffold with cells to form a tissue construct;
   locating the tissue construct on the base of the well in a space defined by the tissue construct support element, the tissue construct being arranged so that it protrudes beyond the upper surface of the support element, and the support element being arranged so that it surrounds the tissue construct;

operating the load applicator to apply a cyclical compressive mechanical load to the tissue construct, to stimulate the deposition of tissue matrix in the tissue construct;

arranging the load applicator so that it at least initially contacts both the tissue construct and the tissue construct support element, so that at least part of a total load generated by the load applicator is borne, at least initially, by the tissue construct support element and the support element deformed by the load applicator;

in which the tissue construct support element has an elastic modulus which is greater than an elastic modulus of the tissue construct prior to commencement of application of the mechanical load.

2. A method as claimed in claim 1, in which the tissue construct is initially subjected to compressive mechanical loading resulting in strains of at least around 10%.

3. A method as claimed in claim 1, in which the load which is applied is a substantially constant magnitude load.

4. A method as claimed in claim 1, in which, upon commencement of cyclical loading, the tissue construct support element bears a majority of the applied load.

5. A method as claimed in claim 4, in which, as more tissue matrix is deposited, the construct becomes thicker and stiffer so that the amount of strain applied to the construct increases.

6. A method as claimed in claim 5, in which the application of the mechanical load continues until the tissue construct bears substantially all of the applied load.

7. A method as claimed in claim 1, in which the mechanical load which is applied to the tissue construct is of a magnitude which results in a strain of at least about 10% in the construct.

8. A method as claimed in claim 1, in which the mechanical load which is applied to the tissue construct is of a magnitude which results in a strain in the range of about 13% to about 23% in the construct.

9. A method as claimed in claim 1, in which the tissue construct comprises at least one anchoring element, which serves for anchoring the tissue engineered construct to tissue in the body of a patient.

10. A method as claimed in claim 9, in which the at least one anchoring element is formed integrally with the scaffold.

11. A method as claimed in claim 1, in which the scaffold is seeded with cells and the resulting construct cultured in culture medium for a period of time prior to being located in the bioreactor.

12. A method as claimed in claim 1, in which the tissue construct support element has a mean thickness, and the tissue construct has a mean thickness which is greater than that of the support element.

13. A method as claimed in claim 1, in which the space is shaped to suit the desired shape of the tissue engineered construct which is to be formed.

14. A method as claimed in claim 1, in which a gap is provided between a wall of the support element and the tissue construct.

15. A method as claimed in claim 1, in which the tissue construct support element has an elastic modulus which is at least around 10 times greater than an elastic modulus of the tissue construct prior to commencement of the application of the mechanical load.

16. A method of repairing human or animal body tissue comprising:

forming an implantable tissue engineered construct in a method comprising the steps of:
providing a bioreactor comprising a well and a load applicator, the well having a base;
locating a resiliently deformable tissue construct support element on the base of the well, the support element having an upper surface;
seeding a scaffold with cells to form a tissue construct;
locating the tissue construct on the base of the well in a space defined by the tissue construct support element, the tissue construct being arranged so that it protrudes beyond the upper surface of the support element, and the support element being arranged so that it surrounds the tissue construct;
operating the load applicator to apply a cyclical compressive mechanical load to the tissue construct, to stimulate the deposition of tissue matrix in the tissue construct;
arranging the load applicator so that it at least initially contacts both the tissue construct and the tissue construct support element,
so that at least part of a total load generated by the load applicator is borne, at least initially, by the tissue construct support element and the support element deformed by the load applicator;
in which the tissue construct support element has an elastic modulus which is greater than an elastic modulus of the tissue construct prior to commencement of application of the mechanical load; and
subsequently implanting the tissue engineered construct in a body of a patient.

17. A method as claimed in claim 16, comprising the further steps of:
determining a location of an area of body tissue where the construct is to be implanted;
assessing a shape of a portion of the tissue to be removed from said location; and
forming the construct with a shape which is appropriate for implantation at said location following removal of said portion of the tissue.

18. A method as claimed in claim 17, comprising implanting a plurality of said tissue engineered constructs at said location.

19. A method as claimed in claim 17, comprising selecting a tissue construct support element defining a space which is appropriate to the shape of the tissue construct which it is desired to form for implantation at said location.

* * * * *